(12) United States Patent
Koneti

(10) Patent No.: US 12,310,568 B2
(45) Date of Patent: May 27, 2025

(54) MULTI-FUNCTIONAL OCCLUDER

(71) Applicant: Nageswara Rao Koneti, Hyderabad (IN)

(72) Inventor: Nageswara Rao Koneti, Hyderabad (IN)

(73) Assignee: NAGESWARA RAO KONETI, Hyderabad (IN)

( * ) Notice: Subject to any disclaimer, the term of this patent is extended or adjusted under 35 U.S.C. 154(b) by 962 days.

(21) Appl. No.: 17/396,795

(22) Filed: Aug. 9, 2021

(65) Prior Publication Data

US 2021/0361270 A1    Nov. 25, 2021

Related U.S. Application Data

(63) Continuation-in-part of application No. 15/759,832, filed as application No. PCT/IN2016/000201 on Aug. 2, 2016, now abandoned.

(30) Foreign Application Priority Data

Sep. 18, 2015   (IN) .......................... 5012/CHE/2015

(51) Int. Cl.
   *A61B 17/00*    (2006.01)
(52) U.S. Cl.
   CPC ................ *A61B 17/0057* (2013.01); *A61B 2017/00597* (2013.01); *A61B 2017/00606* (2013.01); *A61B 2017/00632* (2013.01)

(58) Field of Classification Search
   CPC .......... A61B 17/0057; A61B 17/12022; A61B 2017/00606; A61B 2017/00592; A61B 2017/00867; A61B 2017/00575
   See application file for complete search history.

(56) References Cited

U.S. PATENT DOCUMENTS

| | | | |
|---|---|---|---|
| 5,725,552 A | 3/1998 | Kotula et al. | |
| 5,846,261 A | 12/1998 | Kotula et al. | |
| 5,944,738 A * | 8/1999 | Amplatz | A61B 17/0057 606/213 |
| 6,123,715 A * | 9/2000 | Amplatz | A61F 2/90 606/151 |
| 6,152,935 A * | 11/2000 | Kammerer | A61B 17/083 606/144 |

(Continued)

FOREIGN PATENT DOCUMENTS

| | | |
|---|---|---|
| CN | 1091584 C | 10/2002 |
| CN | 1102373 C | 3/2003 |
| CN | 1106828 C | 4/2003 |

*Primary Examiner* — Phong Son H Dang
(74) *Attorney, Agent, or Firm* — Harita S Achanta

(57) ABSTRACT

The present invention is related to an occlusion device for occluding an opening in a body tissue and a method of deploying said occlusion device to the site of defect. The occlusion device comprises a flexible proximal high-pressure disc and a flexible distal low-pressure disc, that are centrally connected by a central connector section of varying diameter and length which further comprises a stretchable narrow connector at the tapered end, and retention screws. The design of the occlusion device of the present invention is such that it enables haemodynamic adjustment providing a better-fit to the size of the defect, and reduction of clamping force and stress on the conduction system.

5 Claims, 5 Drawing Sheets

(56) References Cited

U.S. PATENT DOCUMENTS

| | | | | |
|---|---|---|---|---|
| 7,223,280 B2* | 5/2007 | Anson | A61B 17/12172 | 606/215 |
| 7,678,123 B2* | 3/2010 | Chanduszko | A61B 17/0057 | 606/139 |
| 7,871,419 B2* | 1/2011 | Devellian | A61B 17/0057 | 606/213 |
| 7,993,392 B2* | 8/2011 | Righini | A61F 2/2436 | 623/2.11 |
| 8,109,946 B2* | 2/2012 | Cahill | A61B 17/0057 | 606/151 |
| 8,579,933 B2* | 11/2013 | Chin-Chen | A61B 17/0057 | 606/213 |
| 8,814,947 B2* | 8/2014 | Callaghan | A61B 17/0057 | 623/23.72 |
| 9,005,242 B2* | 4/2015 | Cahill | A61B 17/0057 | 606/215 |
| 9,138,213 B2* | 9/2015 | Amin | A61B 17/12122 | |
| 9,770,232 B2* | 9/2017 | Amin | A61B 17/0057 | |
| 11,116,486 B2* | 9/2021 | Amplatz | A61B 17/12109 | |
| 2005/0234509 A1* | 10/2005 | Widomski | A61B 17/0057 | 606/213 |
| 2005/0273124 A1* | 12/2005 | Chanduszko | A61B 17/0057 | 606/159 |
| 2005/0273135 A1* | 12/2005 | Chanduszko | A61B 17/0057 | 606/213 |
| 2006/0241690 A1* | 10/2006 | Amplatz | A61B 17/0057 | 606/213 |
| 2007/0010851 A1* | 1/2007 | Chanduszko | A61B 17/0057 | 606/213 |
| 2007/0073337 A1* | 3/2007 | Abbott | A61B 17/0057 | 606/213 |
| 2007/0167981 A1* | 7/2007 | Opolski | A61B 17/0057 | 606/213 |
| 2007/0276415 A1* | 11/2007 | Kladakis | A61B 17/0057 | 606/151 |
| 2009/0062841 A1* | 3/2009 | Amplatz | A61B 17/12159 | 606/200 |
| 2009/0099647 A1* | 4/2009 | Glimsdale | A61B 17/12172 | 623/1.35 |
| 2009/0187214 A1* | 7/2009 | Amplatz | A61B 17/0057 | 606/213 |
| 2011/0054519 A1* | 3/2011 | Neuss | A61B 17/0057 | 606/213 |
| 2013/0066341 A1* | 3/2013 | Ketai | A61B 17/08 | 606/151 |
| 2016/0375186 A1* | 12/2016 | Tuseth | A61M 60/165 | 600/16 |
| 2017/0014113 A1* | 1/2017 | Ma | A61B 17/0057 | |

* cited by examiner

MULTI-FUNCTIONAL OCCLUDER

CROSS-REFERENCE TO RELATED APPLICATIONS

The present application is a continuation-in-part of U.S. patent application Ser. No. 15/759,832, filed Mar. 14, 2018, which itself is a continuation of an International Application Number PCT/IN2016/000201, with a filing date of Aug. 2, 2016, the entire disclosures of which is incorporated herein by reference for all purposes. The present application claims the benefit of foreign priority application number 5012/CHE/2015, with a filing date of Sep. 18 2015, the entire disclosures of which is incorporated herein by reference for all purposes.

FIELD OF INVENTION

The present invention is generally related to an intravascular occlusion device for the treatment of certain medical conditions and, more particularly, related to a multi-functional occlusion device for the treatment of congenital defects.

BACKGROUND OF THE INVENTION

A wide variety of intravascular devices are used in various medical procedures. Certain intravascular devices, such as catheters and guidewires, are generally used to just deliver fluids or other medical devices to specific locations within a patient's body, such as a selective site within the vascular system. Other, frequently more complex, devices are used in the treatment of specific conditions, such as devices used in the removal of vascular occlusions or for the treatment of septal defects and the like.

Congenital heart diseases include patent foramen ovale (PFO), atrial septal defect (ASD), patent ductus arteriosus (PDA), ventricular septal defect (VSD), etc. PFO and ASD are openings in the wall between the right atrium and left atrium of the heart thereby creating the possibility of the passage of blood from the right atrium to the left atrium. But the defect size of PFO is usually smaller than that of ASD and the defect does not extend perpendicularly to the septal wall, i.e. the left atrial septal defect is not concentric with that of the right atrium. Once the occluder has been placed, it prevents the thrombus from entering the left atrium. Furthermore, the atrial septal defect (ASD) is usually larger and requires repair. Currently, there are many types of endocardiac occlusion devices for the treatment of congenital heart diseases. These occluders are delivered to the desired location using a corresponding catheter.

Several devices such as the Amplatzer Septal Occluder, Gore Helex Septal Occluder and Occlutech Figula have been developed to occlude these defects. The Amplatzer design, disclosed in U.S. Pat. Nos. 5,725,552, 5,846,261, 5,944,738 and 6,123,715, has braided and woven nitinol wires that are shape set into two discs with a thinner middle portion, such that the middle portion is placed through the opening and the two discs clamp down on each side of the body tissue.

In the past, mechanical occlusion devices have been proposed for the treatment of congenital heart diseases, some of which have an accurate diameter of the defect to be closed while in certain cases, it may not always be correct in all clinical situations such as Perimembranous Ventricular septal defect (Pm VSD), para-valvular leak and Coronary arterio-venous fistula (CAVF). The physician tends to use an over-sized device to prevent embolization or residual leak. This over-sizing may lead to complications such as heart blocks, distortion of the device and damage to the intra- or extra-cardiac structures. However, these devices may be difficult to adapt to a variety of short and long tunnel widths.

Prior to implantation of these devices, it is important to determine the thickness of the septal wall near the defect and the approximate width of the defect, in order to provide an appropriately sized device. A balloon catheter and a calibrated guidewire having radiopaque regions of known length, may be utilized by a physician during a preliminary fluoroscopic procedure to estimate the defect's size, shape and thickness of the septal wall near the defect. Although useful, the exact size and shape of the defects cannot be determined, thereby increasing the possibility of leakage around the occluding device. Hence, a device that inherently adjusts to the shape and thickness of the defect would be desirable.

Further, the shapes (for example squares, triangles, pentagons, hexagons and octagons) of the devices in the prior art require a larger surface contact area and have corners which may extend to the free wall of the atria. Each time the atria contracts (approximately 100,000 times per day), the corners extending to the atria walls are bent, thus creating structural fatigue fractures in approximately 30 percent of all cases. Furthermore, the previous devices require a French 14-16 introducing catheter, making it impossible to treat children affected with congenital defects using these devices. Hence, it would be advantageous to provide a reliable embolization device which is both easy to deploy through a 6-7 French catheter and which automatically adjusts to the shape and thickness of the defect.

CN 1106828, CN 1091584 and CN1102373 disclose mechanical occlusion devices for the treatment of congenital heart diseases. Such devices include a support mesh with contractibility and biocompatible materials that are connected to the circumference of the support mesh. The support mesh, which is first placed in the catheter, is delivered to the desired location, and is then deployed to close the septal defect. Such devices are easy to withdraw and have excellent centricity. However, the left disc of such devices directly contacts the blood, and can potentially form a thrombus and release harmful metallic elements more easily. Moreover, as the two discs are integrated, they cannot automatically adjust angularly to adapt to the unique anatomy of the patient. Meanwhile, if the left disc is not deployed completely, the operation becomes more complicated.

In addition, with the existing techniques and operation methods, it is very difficult to determine the size and shape of the septal defect precisely, and with the limiting waist size, difficulties such as selection error are encountered by the physicians. If an oversized device is selected, the occluder will form a cucurbit shape and result in an imperfect closing effect.

Considering the above stated difficulties associated with occlusion procedures and devices available in the prior art, there is a strong need for devices that are more effective and can provide a constant inward axial pressure on each side of the body tissue. Although some of these devices are adequate, there is a need for devices that provide a more effective fit and grip for a variety of openings.

The devices disclosed herein are designed to address these and other drawbacks of prior art septal closure devices.

OBJECT OF THE INVENTION

It is accordingly a principal object of the present invention to provide a device suitable for occluding various septal defects.

Another object of the present invention is to provide an occluding device that has multi-functionality and can be applicable for various defects of different sizes.

Yet another object of the invention is to provide an occluder with a haemodynamic advantage to adjust according to the size of the defect thereby providing an excellent fit.

These and other objects, of the present invention will become readily apparent to those skilled in the art from a review of the following detailed description of the preferred embodiment in conjunction with the accompanying claims and drawings in which numerals in the several views refer to corresponding parts.

SUMMARY OF THE INVENTION

The present invention is related to an intravascular occlusion device for the treatment of certain medical conditions and more particularly, related to a multi-functional occlusion device for the treatment of congenital defects such as Atrial and Ventricular Septal Defects (ASD and VSD respectively), Perimembranous Ventricular septal defect (Pm VSD), Pm VSD with membranous septal aneurysm, Muscular VSD, Post-operative residual VSD, Coronary arterio-venous fistula (CAVF), Systemic arterio-venous fistula (SAVF), Systemic to pulmonary collaterals, Rupture of sinus of Valsalva (RSOV), selected cases of aorto-pulmonary window as well as conditions that result from previous medical procedures such as Para-Valvular Leaks (PVL) following surgical valve repair or replacement. More particularly, the device has the ability to adjust haemodynamically as per the clinical situation.

The present invention is related to an occlusion device comprising of two uniform discs: a proximal high-pressure disc and a distal low-pressure disc; a central connector section which is continuous with said high-pressure disc, and further comprises a stretchable narrow connector; and a plurality of retention screws. Said proximal high-pressure disc and said distal low-pressure disc are held in place using retention screws. Said retention screws are located on either side of the discs. Said discs of the occlusion device are held together through a central connector section which has varying diameter and length, and is conical in shape. The broader end of said central connector section is continuous with said high-pressure disc and the tapered end of said central connector section comprises a stretchable narrow connector. Said stretchable narrow connector of said central geometrically shaped connector section connects said central geometrically shaped connector section of the proximal high-pressure disc with the distal low-pressure disc. The conical connector section which has a tapering diameter lends a hemodynamic advantage.

The present invention is also related to a method for occluding an opening in a body tissue by deploying an occlusion device to the required site. The method comprises the deployment of the occlusion device through the trans-venous approach or trans-arterial approach also known as antegrade and retrograde methods, respectively, which is possible due to the design of the occluder device of the present invention.

Further features and advantages of the present disclosure will become apparent from consideration of the following description and the appended claims when taken in conjunction with the accompanying drawings. It should be understood that the description and specific examples are intended for purposes of illustration only and are not intended to limit the scope of the present disclosure.

DETAILED DESCRIPTION

The present invention is related to devices intended to occlude an aperture within a body tissue. The term "occlusion device" in the present disclosure is meant for the interpretation of the device for occluding a defect in a living body. The terms "occlusion device", "occluding device", and "occluder" are interchangeably used in the present application. The terms "central connector section", "conical connector section", "conical connection section", "central conically shaped connector section", and "central geometrically shaped connector section" are interchangeably used in the present application. In particular and as described in detail below, the described multifunctional occlusion device may be used for closing various septal defects in the heart. The occlusion device comprises of two uniform discs: a proximal high-pressure disc and a distal low-pressure disc that are held in place using retention screws on either side. Said proximal disc and said distal disc are interconnected through a central connector section which according to some embodiments may be a conical structure. Said central connector section further comprises a narrow connector that is integrally connected to the central connector section at its tapered end. The multi-functional occlusion device of the present invention comprises a proximal high-pressure disc which is continuous with the central connector section at the broader end of the central connector section, and a distal low-pressure disc which is connected to the narrow connector present at the tapered end of the central connector section, thus functioning as high-pressure disc and low-pressure disc, respectively. The varying diameter and length of said central geometrically shaped connector section of said proximal high-pressure disc straddles said high-pressure disc in the high-pressure chamber of the heart, and said low-pressure disc in the low-pressure chamber of the heart, whereby it provides stability on opposite sides of a defect, and hemodynamic adjustment is achieved with the septal defect. The proximal high-pressure disc and the distal low-pressure disc are positioned in the ventricular and arterial sections respectively.

Figure 1:
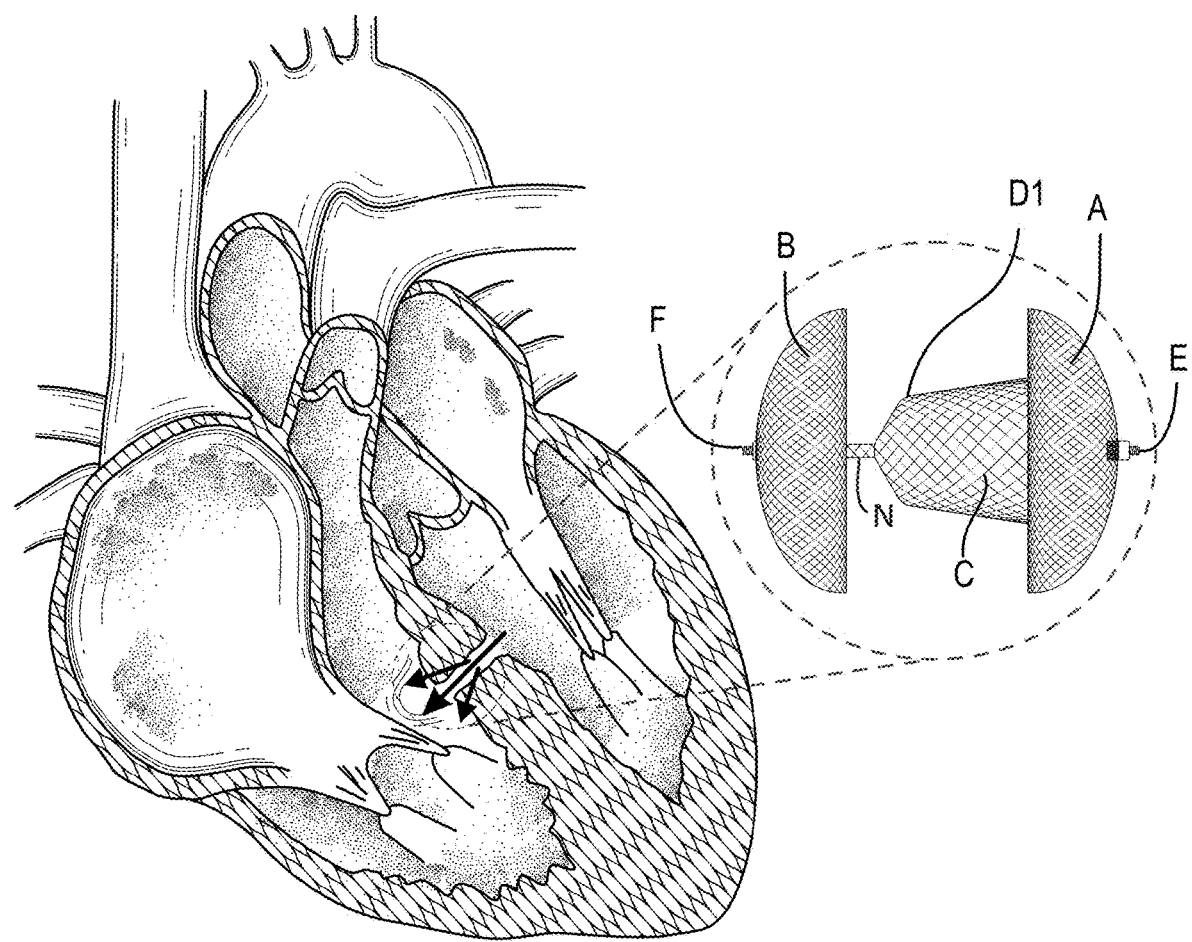
FIG. 1 is a human heart with a ventricular septal defect wherein the present invention is used in accordance with some embodiments of the present disclosure.

FIG. 1 illustrates a human heart having a right atrium, a left atrium, and a ventricular septal defect.

Figure 2:
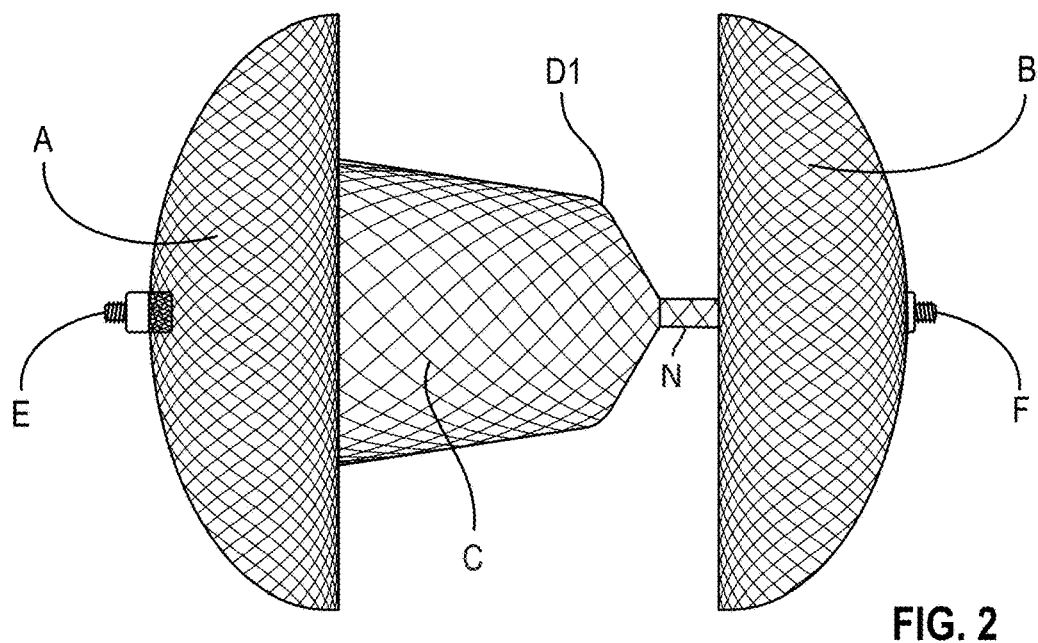
FIG. 2 is a perspective view of an occlusion device of the present invention.

FIG. 2 illustrates the occlusion device of the present invention for use in occluding an abnormal opening in a patient's body. In an embodiment, the occlusion device comprises of two uniform disc-shaped portions 'A' & 'B' connected through a central connector section 'C' having a stretchable narrow connector 'N'. Said discs are proximal high-pressure disc and distal low-pressure disc respectively. Said discs can be deployed on either side depending on the clinical situation.

Figure 2A:
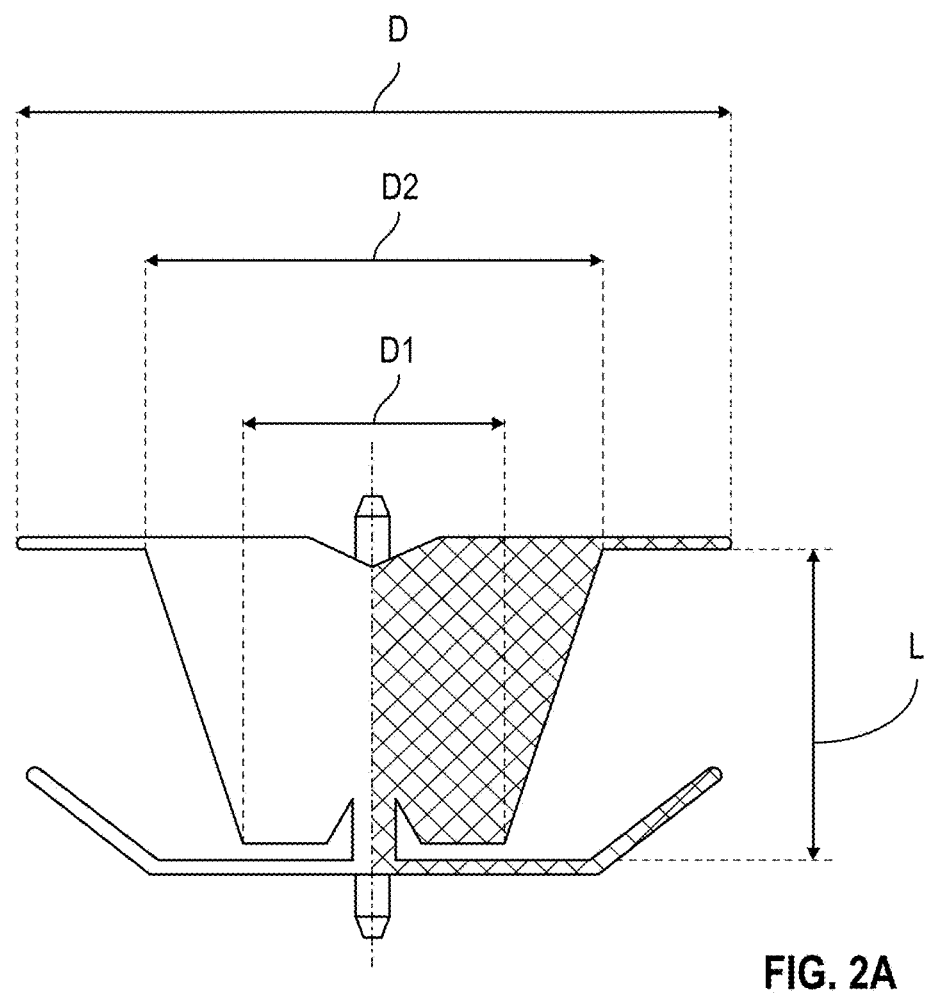
FIG. 2A illustrates the basic design of the present invention.

FIG. 2A further illustrates the basic design of the occlusion device of the present invention, wherein "D" represents the overall diameter of the device, "D1" represents the diameter at the tapered lower end, "D2" represents the diameter at the maximum end, and "L" represents the length of the device.

Figure 3:
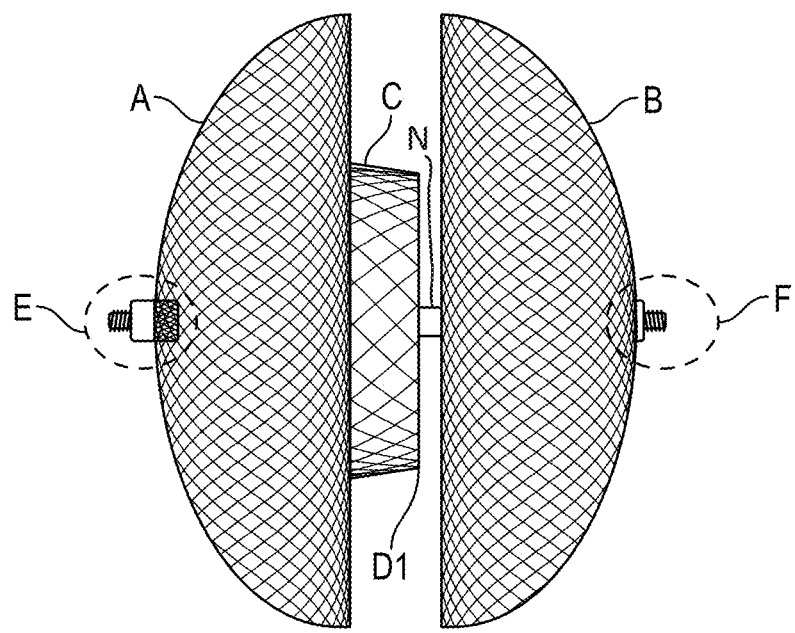
FIG. 3 is a perspective view of an occlusion device which comprises two disc-shaped portions along with retention screws.

FIG. 3 illustrates the occlusion device comprising of two disc-shaped portions with two retention screws 'E' & 'F'. Said retention screws present on either side of the discs aid in the retention of the discs in place after the deployment on the side of choice, which depends on the clinical situation.

Figure 4:
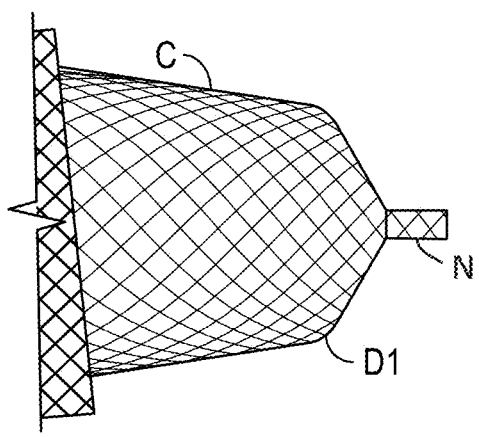
FIG. 4 illustrates the central connector section as a conical structure which further comprises a narrow connector which connects the proximal high-pressure disc and the distal low-pressure disc.

FIG. 4 illustrates the connectivity between the proximal high-pressure disc 'A' and distal low-pressure disc 'B' through said narrow connector 'N' of said central connector section 'C'. The central connector section presented in FIG. 2A is a conical structure with varying diameters with the diameter decreasing from 'D' to 'D2' to 'D1'. The conical structure determines the size of the device. The length of the conical structure is variable depending on the situation, and can be customized. The diameter of the conical structure can range, but not limiting to, for example, from a maximum of a 7/5 device at the broader end being 7 mm which tapers to 5 mm at "D1".

According to an embodiment, the occluder of the present invention has the ability to be adjusted in the high-pressure chamber as per the required diameter at the site of defect. The determination of the diameter of the defect that is to be closed may not always be accurate in all clinical situations, particularly in situations such as Pm VSD, para-valvular leak and CAVF. The physician tends to use an over-sized device to prevent embolization or residual leak. This may lead to oversizing related complications such as heart blocks, distortion of device and damage to intra- or extra-cardiac structures. This is solved by said conical structure of the central connector section, and said narrow connector of the present invention that lend a haemodynamic advantage to adjust according to the size of the defect. The incremental diameter of the central connector section allows the device to fit in the defect as per the desired diameter by pressure adjustment. The high-pressure disc adjusts into the defect by the lateral pressure of the systemic side of the chamber of the heart. The occlusion device of the present invention is a self-adjustable device, and therefore fits into the defect or anatomical structure when deployed in a desired location. The device will straddle itself to the septum or vessel wall by the lateral pressure in the chamber.

According to a preferred embodiment, this hemodynamic advantage enables the placement of the proximal high-pressure disc in the high-pressure chamber and the distal low-pressure disc in the low-pressure chamber, based on the clinical situation.

The central connector section 'C' can be adjusted as per the diameter of the defect after positioning within the desired position to close. The high pressure in the cardiac chamber pushes the device to the desired diameter and adjusts according to the diameter. This haemodynamic advantage aligns the device properly within the defect, and prevents oversizing and thus associated complications.

The discs of the occlusion device are of uniform size, and comprise retention screws on the outer side, which hold the deployed disc in the deployed position, thus enabling deployment of the device through the trans-venous approach called as antegrade method or a trans-arterial approach called retrograde approach.

Figure 5:
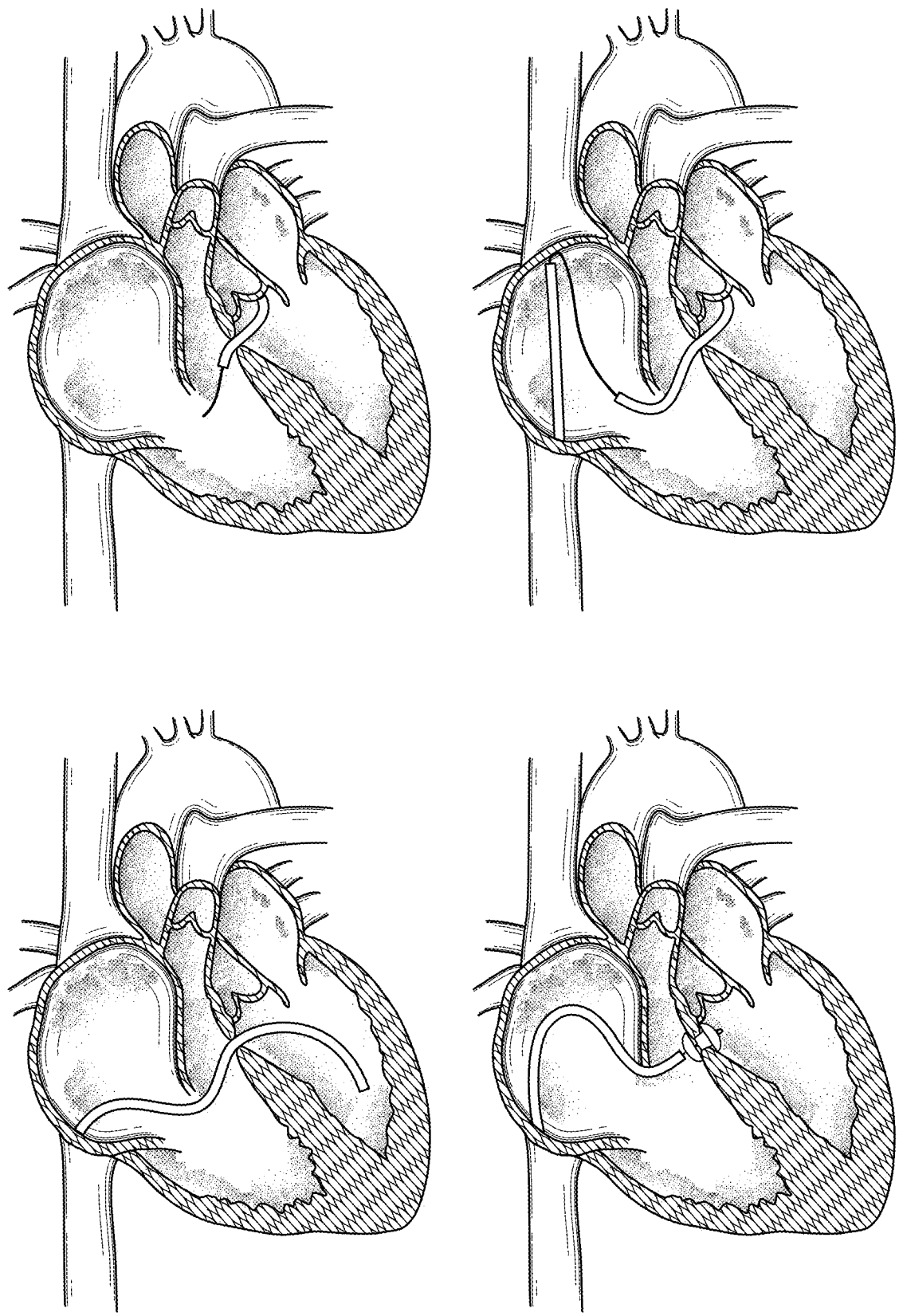
FIG. 5 illustrates the method of deployment of the occlusion device in the patient body through antegrade approach.

FIG. 5 illustrates a method of deploying the occlusion device of the present invention in a patient's body employing an antegrade approach. The antegrade approach involves forming an arterio-venous looping, and is applicable for the closure of defects such as the left to right shunts, fistulae and para-valvular leaks.

Figure 6:
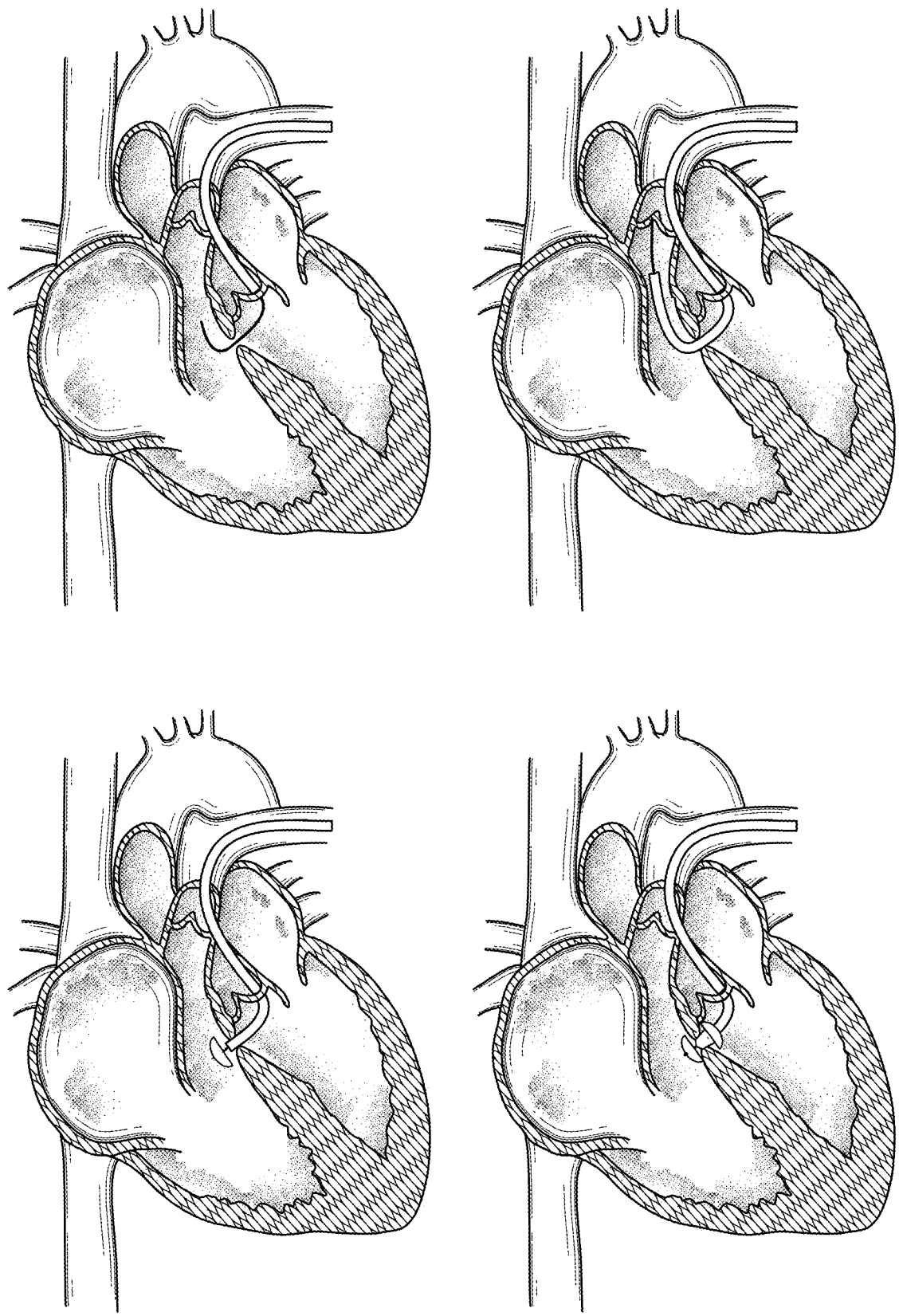
FIG. 6 illustrates the method of deployment of the occlusion device in the patient body through retrograde approach.

FIG. 6 illustrates a method of deploying the occlusion device of the present invention in a patient's body employing a retrograde approach (trans-arterial approach). The retrograde approach is simple, and applicable for the closure of defects such as Pm VSDs, CAVF, SAVF and other variety of conditions.

According to an embodiment, the device can either have a membrane or not have a membrane. According to yet another embodiment, the membrane can be a PTFE membrane. According to a preferred embodiment, there is no membrane for the sizes 5/3-8/6, whereas a PTFE membrane is used for the sizes 9/7-14/12.

Table 1 illustrates the basic design and the variations in size, which are only illustrative and non-limiting examples. Modifications can be made as per the clinical situation and be customized.

TABLE 1

Design and variables of a multi-functional occluder

| Size | D | D1 | D2 | L | Recommended Sheath | Membrane |
|---|---|---|---|---|---|---|
| LT-5-3 | 10 | 3 | 5 | 4 | 5F | No |
| LT-6-4 | 10 | 4 | 6 | 4 | 5F | No |
| LT-7-5 | 12 | 5 | 7 | 4 | 5F-6F | No |
| LT-8-6 | 12 | 6 | 8 | 4 | 5F-6F | No |
| LT-9-7 | 14 | 7 | 9 | 4 | 7F | Yes |
| LT-10-8 | 14 | 8 | 10 | 4 | 7F | Yes |
| LT-12-10 | 16 | 10 | 12 | 4 | 7F | Yes |
| LT-14-12 | 18 | 12 | 14 | 4 | 7F | Yes |

The aforementioned table lists the various sizes of the device and diameter, according to some of the embodiments of the present invention.

Example 1: The LT-5/3 device has 5 mm as the maximum diameter at "D2" and 3 mm minimum diameter at the tapering end "D1". The length of the device is 4 mm and the recommended sheath for the device is 5F. There is no membrane present for this size.

Example 2: The LT-6/4 device has 6 mm maximum diameter at "D2" and 4 mm minimum diameter at lower end "D1". The length of the device is 4 mm and the recommended sheath for the device is 5F. There is no membrane present for this size.

Example 3: The LT-7/5 device has 7 mm maximum diameter at "D2" and 5 mm minimum diameter at lower end "D1". The length of the device is 4 mm and the recommended sheath for the device is 5F-6F. There is no membrane present for this size.

Example 4: The LT-8/6 device has 8 mm maximum diameter at "D2" and 6 mm minimum diameter at lower end "D1". The length of the device is 4 mm and the recommended sheath for the device is 5F-6F. There is no membrane present for this size.

Example 5: The LT-9/7 device has 9 mm maximum diameter at "D2" and 7 mm minimum diameter at lower end "D1". The length of the device is 4 mm and the recommended sheath for the device is 7F. PTFE membrane is present for this size.

Example 6: The LT-10/8 device has 10 mm maximum diameter at "D2" and 8 mm minimum diameter at lower end "D1". The length of the device is 4 mm and the recommended sheath for the device is 7F. PTFE membrane is present for this size.

Example 7: The LT-12/10 device has 12 mm maximum diameter at "D2" and 10 mm minimum diameter at lower end "D1". The length of the device is 4 mm and the recommended sheath for the device is 7F. PTFE membrane is present for this size.

Example 8: The LT-14/12 device has 14 mm maximum diameter at "D2" and 12 mm minimum diameter at lower end "D1". The length of the device is 4 mm and the recommended sheath for the device is 7F. PTFE membrane is present for this size.

According to an embodiment of the present invention, a shape memory alloy suitable such as Ni—Ti available under the more commonly known name Nitinol (Nickel and Titanium alloy), may be used for the manufacture of the occlusion device. The standard technique for manufacturing the device is Nitinol wire (0.0020"~0.0026" wire) and molded.

The present invention is related to a multi-functional occluding device comprising of two uniform flexible discs which possess retention screws on the outer sides, and are connected by a central conically shaped connector section having a stretchable narrow connector. The presence of the retention screws on the outer sides enables deployment of the device at the site of the defect from either the antegrade or retrograde approach. The multi-functional occluding device of the present invention may be deployed from the venous side by positioning the proximal high-pressure disc first in the systemic side and then positioning the distal low-pressure disc in the venous side. Alternately, said multi-functional occluding device of the present invention may be deployed in an arterial approach, wherein the distal low-pressure disc is first positioned in the venous side and then the proximal high-pressure disc is positioned in the systemic side.

The central conically shaped connector section which possesses tapering diameters, renders the advantages of hemodynamic adjustment of the discs of the occlusion device to provide a better-fit, leak-proof occlusion of the defect site; customization; and ease of handling either by a left-handed or right-handed approach.

According to the embodiments of the present invention, the stretchable narrow connector of said central geometrically shaped connector section is flexible. The longitudinal stretchability of said narrow connector eliminates clamping force. The lateral stretchability of said narrow connector eliminates shear stress on the conduction system. The advantages of the central connector section and narrow connector include hemodynamic adjustment, minimizing or eliminating clamping stress by the device on the electrical conduction system during the closure of defect, minimizing or eliminating complications such as formation of heart blocks and/or hemolysis, distortion of the device, and damage to intra- or extra-cardiac structures.

The present invention is related to multi-functional occlusion device comprising of: a flexible proximal high-pressure disc positioned in the high-pressure chamber of heart, and a flexible distal low-pressure disc positioned in the low-pressure chamber of heart; retention screws on the outer side of said proximal high-pressure disc and said distal low-pressure disc; and a central geometrically shaped connector section comprising a narrow connector; wherein said proximal high-pressure disc and said distal low-pressure disc are of uniform size, and straddle with the septum of the heart to provide stability on opposite sides of a defect; and said central geometrically shaped connector section is of varying diameter and length, and provides hemodynamic adjustment of said proximal high-pressure disc and said distal low-pressure disc. Said central geometrically shaped connector section that has a variable size and length, and has the broader end continuous with said proximal high-pressure disc and a stretchable narrow connector at the tapered end, connects the distal low-pressure disc through the narrow connector, thus enabling a tight fit depending on the defect size. The stretchable property of said narrow connector section, eliminates clamping force and stress on the conduction system.

The aforementioned described features help alleviate the problems such as heart blocks, due to increased shear stress due to radial force and clamping force by the two discs of the occluder, associated with prior art technologies. It will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

It is to be understood, however, that the present invention would not be limited by any means to the parts, arrangements and materials that are not specifically described, and any change to the materials, variations, sizes and modifications can be made without departing from the spirits and scope described in the present invention.

The invention claimed is:

1. A multi-functional occlusion device comprising of:
   a flexible proximal high-pressure disc and a flexible distal low-pressure disc;
   retention screws on the outer side of said proximal high-pressure disc and said distal low-pressure disc; and
   a central geometrically shaped connector section of varying diameter and length which is continuous with the proximal high-pressure disc at a broader end, and further comprises a stretchable narrow connector at a tapered end, wherein,
   the central geometrically shaped connector section is configured to straddle said high-pressure disc in the high-pressure chamber of the heart and said low-pressure disc in the low-pressure chamber of the heart,
   and said narrow connector of said central geometrically shaped connector section connects said central geometrically shaped connector section of said proximal high-pressure disc with said distal low-pressure disc.

2. The multi-functional occlusion device according to claim 1, wherein said proximal high-pressure disc and said distal low-pressure disc are of uniform size.

3. The multi-functional occlusion device according to claim 1, wherein the varying diameter and length of said central geometrically shaped connector section configured to straddle said high-pressure disc in the high-pressure chamber of the heart and said low-pressure disc in low-pressure chamber of heart, provides stability on opposite sides of a defect, and achieves hemodynamic adjustment with the septal defect due to its varying diameter and length.

4. The multi-functional occlusion device according to claim 1, wherein said narrow connector of said central geometrically shaped connector section is flexible, and the stretchability of said narrow connector eliminates clamping force and stress on the conduction system.

5. The multi-functional occlusion device according to claim 1, wherein said device may or may not include a membrane.

\* \* \* \* \*